United States Patent [19]
Birdsall et al.

[11] Patent Number: 5,817,152
[45] Date of Patent: Oct. 6, 1998

[54] CONNECTED STENT APPARATUS

[76] Inventors: Matthew Birdsall, 2561 Barona Pl., Santa Rosa, Calif. 95405; Bradley Jendersee, 1848 Castle Dr., Petaluma, Calif. 94954; Robert Lashinski, 409 Princess Way, Windsor, Calif. 95492; Michael D. Boneau, 993-6 Asilomar Ter., Sunnyvale, Calif. 94086

[21] Appl. No.: 451,270

[22] Filed: May 30, 1995

Related U.S. Application Data

[63] Continuation-in-part of Ser. No. 326,024, Oct. 19, 1994, abandoned.

[51] Int. Cl.⁶ ........................................................ A61F 2/06
[52] U.S. Cl. .................................. 623/1; 623/12; 606/195
[58] Field of Search .................................... 623/1, 11, 12; 606/191–200

[56] References Cited

U.S. PATENT DOCUMENTS

| | | |
|---|---|---|
| 5,035,706 | 7/1991 | Gianturco et al. ...................... 606/198 |
| 5,102,417 | 4/1992 | Palmaz ..................................... 606/195 |
| 5,104,404 | 4/1992 | Wolff ............................................. 623/1 |
| 5,135,536 | 8/1992 | Hillstead ................................. 606/195 |
| 5,195,984 | 3/1993 | Schatz ..................................... 606/195 |
| 5,421,955 | 6/1995 | Lau et al. ................................ 606/198 |
| 5,449,373 | 9/1995 | Pinchasik et al. ...................... 606/198 |
| 5,514,154 | 5/1996 | Lau et al. ................................ 606/195 |

*Primary Examiner*—Debra S. Brittingham
*Attorney, Agent, or Firm*—Richard L. Klein

[57] ABSTRACT

An endoprosthetic device comprises at least two short stent segments welded together to form a connected stent. Each stent segment defines a single wire having straight sections integrally formed between axial turns. The welds are placed between stent segments at one or more aligned adjacent axial turns. The welded connected stent is flexible enough to allow it to pass through sharp turns and to be implanted to conform to the contour of the lesion to be treated. In one aspect of the invention all adjacent axial turns are welded together. In another aspect of the invention, selected adjacent axial turns are welded together to create a generally balanced spiral pattern of welds surrounding the cylindrical connected stent.

14 Claims, 4 Drawing Sheets

CONNECTED STENT APPARATUS

This application is a continuation-in-part of U.S. Pat. application Ser. No. 08/326,024, filed on Oct. 19, 1994 now abandoned.

FIELD OF THE INVENTION

This invention relates to medical implant devices, and more specifically to a connected implantable stent apparatus consisting of at least two short stent segments connected by welding, or by using other methods producing substantially rigid joints, and particularly suitable for the treatment of coronary or peripheral vessels in humans.

BACKGROUND OF THE INVENTION

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

An important development for treating atherosclerosis and other forms of coronary narrowing is percutaneous transluminal coronary angioplasty, hereinafter referred to as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

Angioplasty is typically performed as follows: A thin walled hollow guiding catheter is introduced into the body via a relatively large vessel, such as the femoral artery in the groin area or the brachial artery in the arm. Access to the femoral artery is achieved by introducing a large bore needle directly into the femoral artery, a procedure known as the Seldinger Technique. Once access to the femoral artery is achieved, a short hollow sheath is inserted to maintain a passageway during the procedure. The insertion of the flexible guiding catheter involves the negotiation of an approximately 180 degree turn through the aortic arch to allow the guiding catheter to descend into the aortic cusp where entry may be gained to either the left or the right coronary artery, as desired.

After the guiding catheter is advanced to the ostium of the coronary artery to be treated by angioplasty, a flexible guidewire is inserted into the guiding catheter through a balloon (described infra) and advanced to the area to be treated. The guidewire provides the necessary steerability for passage through the lesion. The guidewire is advanced across the lesion, or "wires" the lesion, in preparation for the advancement of a balloon catheter composed of polyethylene, polyvinyl chloride, polyolefin, or other suitable substance across the guide wire. The balloon, or dilatation, catheter is placed into position by sliding it along the guide wire. The use of the relatively rigid guide wire is necessary to advance the catheter through the narrowed lumen of the artery and to direct the balloon, which is typically quite flexible, across the lesion. Radiopaque markers in the balloon segment of the catheter facilitate positioning across the lesion. The balloon catheter is then inflated with contrast material to permit fluoroscopic viewing during treatment. The balloon is alternately inflated and deflated until the lumen of the artery is satisfactorily enlarged.

Unfortunately, while the affected artery can be enlarged, in some instances the vessel restenoses chronically, or closes down acutely, negating the positive effect of the angioplasty procedure. In the past, such restenosis frequently necessitated repeat PTCA or open heart surgery. While such restenosis does not occur in the majority of cases, it occurs frequently enough that such complications comprise a significant percentage of the overall failures of the PTCA procedure, for example, twenty-five to thirty-five percent of such failures.

To lessen the risk of restenosis, various devices have been proposed for mechanically keeping the affected vessel open after completion of the angioplasty procedure. Such mechanical endoprosthetic devices, which are generally referred to as stents, are typically inserted into the vessel, positioned across the lesion, and then expanded to keep the passageway clear. Effectively, the stent overcomes the natural tendency of the vessel walls of some patients to close back down, thereby maintaining a more normal flow of blood through that vessel than would be possible if the stent were not in place.

Various types of stents have been proposed, although to date none has proven completely satisfactory. One proposed stent involves a tube of stainless wire braid. During insertion, the tube is positioned along a delivery device, such as a catheter, in a compressed configuration which extends the tube along the catheter, making the tube diameter as small as possible. When the stent is positioned across the lesion, it is expanded, causing the length of the tube to contract and the diameter to expand. Depending on the materials used in construction of the stent, the tube maintains the new shape either through mechanical force or otherwise The Palmaz stent (U.S. Pat. No. 4,733,665) involves what may be thought of as a stainless steel cylinder having a number of slits in its circumference, resulting in a mesh when expanded. The stainless steel cylinder is delivered to the affected area by means of a balloon catheter, and is then expanded to the proper size by inflating the balloon.

Significant difficulties have been encountered with known prior art stents, including failure to readily conform to the vessel shape, and including lack of flexibility which is required to track through, and to be implanted in, tortuous vascular anatomy. In addition, the relatively long length of most prior art stents has made it difficult to treat curved vessels, and has also effectively prevented successful implantation of multiple stents.

One solution to this problem is to implant short discrete stent segments that would make up the length of the stenosis to be stented. However, short stent segments have proven to be somewhat unstable with respect to positional stability. These and other complications have resulted in a low level of acceptance for such stents within the medical community, and to date stents have not been accepted as a practical method for treating chronic restenosis.

Boneau U.S. Pat. No. 5,292,331 provides a unitary wire-like stent structure configured to form a plurality of upper and lower axial peaks, and is delivered and expanded in a manner similar to delivery of the prior art stents described above. The low mass and relatively short length of the Boneau stent increased steerability through curved vessels. Copending U.S. Pat. application Ser. No. 08/326,024 describes methods of connecting one or more Boneau stents using suture materials, short lengths of wire or ribbon, and internally or externally mounted sleeves.

SUMMARY OF THE INVENTION

A connected stent embodying the principles of the present invention defines an endoprosthetic device or single stent comprised of at least two short stent segments interconnected by welding, or by other methods producing a substantially rigid joint, for example soldering, rigid adhesive, etc. to enable selection of a stent tailored to the dimensions of the lesion to be treated, and to maintain positional stability within the vasculature. Interconnection of discrete stent segments occurs preferably by welding corresponding axial turns, or crowns, on aligned adjacent stent segments.

Alternatively, for increasing the flexibility of three or more welded stent segments, the number of welds is decreased by welding in a substantially spiral, or alternating pattern which does not include welds at all adjacent crowns. In this embodiment, the stent segments themselves are sufficiently flexible to enable the connected stent to maneuver through and conform to the often tortuous vessels requiring treatment. The preferred embodiment uses stent segments having four crowns at each end with welds at each adjacent crown area of the connected stent. The stent segments having at least one pair of axially aligned adjacent crown areas.

In broadest terms, the connected endovascular stent apparatus of this invention provides a plurality of short discrete stent segments each forming a cylinder, each cylinder having an inside, outside, and at least one end surface, with at least one set of axial turns, or crowns, on corresponding end surfaces on adjacent stent segments connected by a method producing a substantially rigid joint between crowns. The inventive stent apparatus may be formed from a plurality of single pieces of wire, each formed into sections to define an expandable stent, and joined together as described herein. The resultant stent apparatus can then be compressed onto a balloon catheter, delivered to the affected vessel and expanded in place, all as described herein. Additionally, multiple connected stents can be spaced apart and compressed onto a balloon catheter for delivery to the affected vessel.

The stent, or endovascular support device, of the present invention may preferably be comprised of implantable quality high grade stainless steel or other implantable material, machined specially for intravascular applications. The inventive stent segments may comprise a plurality of circles or ellipsoids formed to create a plurality of axial bends, thereby permitting compression of the connected stent onto a delivery catheter, and subsequent expansion once in place at the affected area.

The deployment methods for the connected inventive stent apparatus may include balloon expanding, self-expanding, self-retracting, and mechanically expanding. Some of the intended uses include PTCA type stenting, PTA type stenting, graft support, graft delivery, INR use, GI tract use, drug delivery, and biliary stenting.

A general object of the present invention is to provide a connected stent that overcomes the drawbacks and limitations of the prior art.

A specific object of the present invention is to provide a connected stent comprised of at least two, short stent segments connected by a method producing a substantially rigid joint and having a length sufficient to maintain positional stability when implanted.

Another specific object of the present invention is to provide a connected stent comprised of short stent segments of low mass formed of straight segments integrally joined at axial bends (crowns) wherein individual, adjacent short segments are welded together at one or more adjacent crowns.

One more specific object of the present invention is to provide a connected stent comprised of at least three short stent segments wherein the welds form a spiral or alternating pattern around the generally circular, or elliptical, connected stent thereby welding at a single adjacent crown area in each plane of the stent.

An additional object of the present invention is to provide a connected, welded stent having stent segments sufficiently flexible so that a spiral or alternating pattern of rigid welds allows the connected stent to be maneuvered through and implanted in highly curved vessels.

Yet another object of the present invention is to provide a connected stent made from a plurality of short stent segments to enable a single connected stent, or multiple connected stents, to be tailored to the dimensions of the particular area to be treated.

These and other objects, advantages and features of the present invention will become more apparent upon considering the following detailed description of a preferred embodiments, presented in conjunction with the accompanying drawings.

DETAILED DESCRIPTION OF PREFERRED EMBODIMENTS

Figure 1:
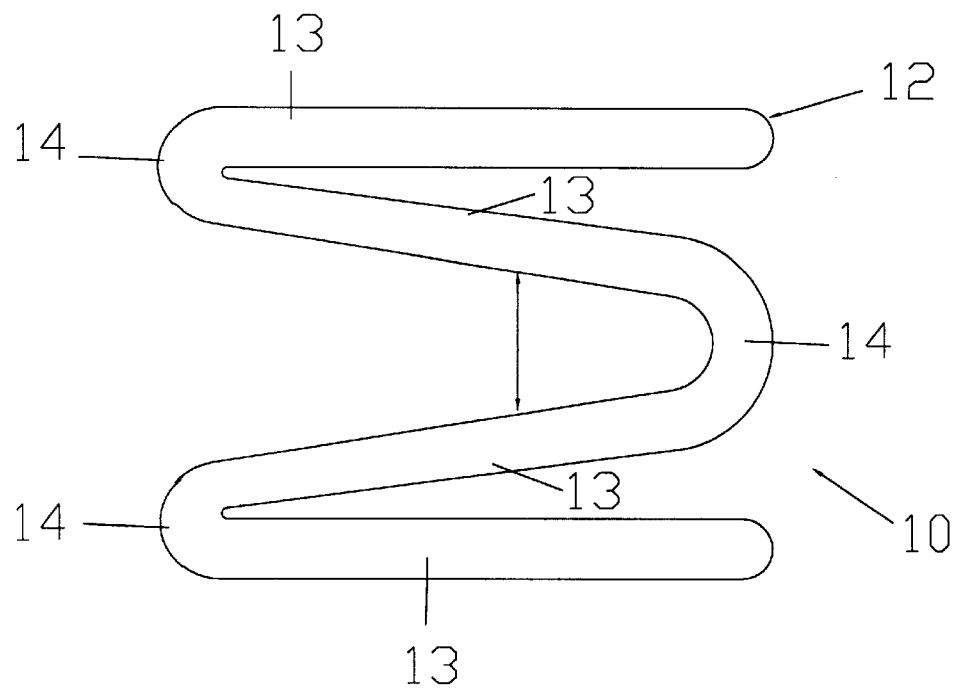
FIG. 1 is a side sectional view of a stent segment in its expanded configuration taken along lines 2—2 in FIG. 2.
Figure 2:
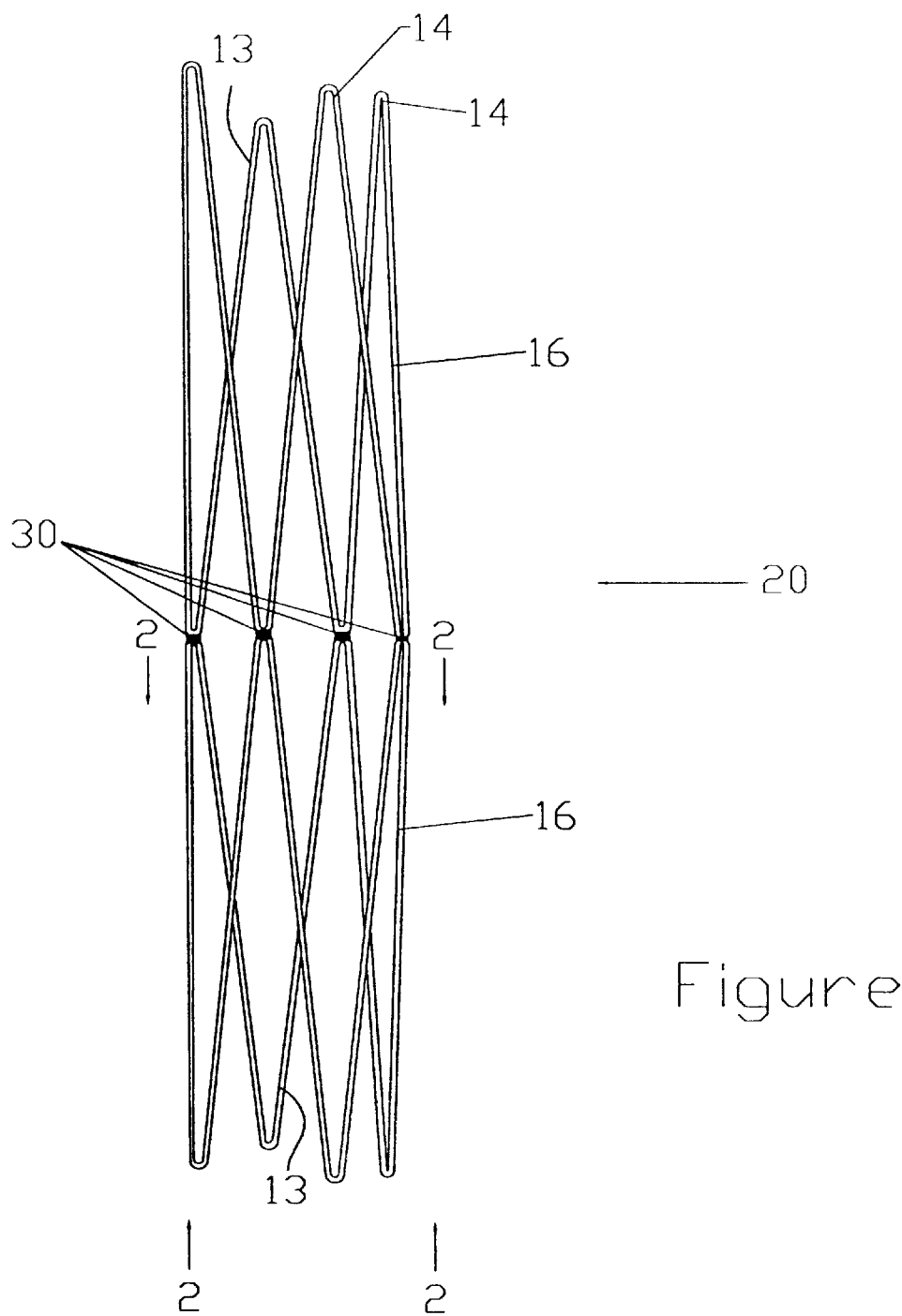
FIG. 2 is a side elevational view of a connected stent embodying principles of the present invention and showing two, short, discrete stent segments of FIG. 1 connected at adjacent axial turns, or crowns, by welds.

FIG. 1 is a side sectional view of a preferred stent segment 10 for forming a connected stent embodying the principles of the present invention. The stent segment 10 comprises a single wire 12 bent into a plurality of straight sections 13 integrally joined by discrete axial turns, or crowns 14 and forming a cylinder 16, as best shown in FIG. 2. In the preferred stent segment 10, the straight sections 13 and the crowns 14 have substantially the same cross-sectional dimensions.

The stent segment 10 is preferable formed from implantable materials having good mechanical strength, such as implantable quality stainless steel wire. The outside of the stent segment may be selectively plated with platinum or other radiopaque materials to provide improved visibility during fluoroscopy. The cross-sectional shape of the finished stent segment 10 may be circular, ellipsoidal, rectangular, hexagonal, square, or another polygon, although at present it is believed that circular or ellipsoidal may be preferable.

Figure 3A:
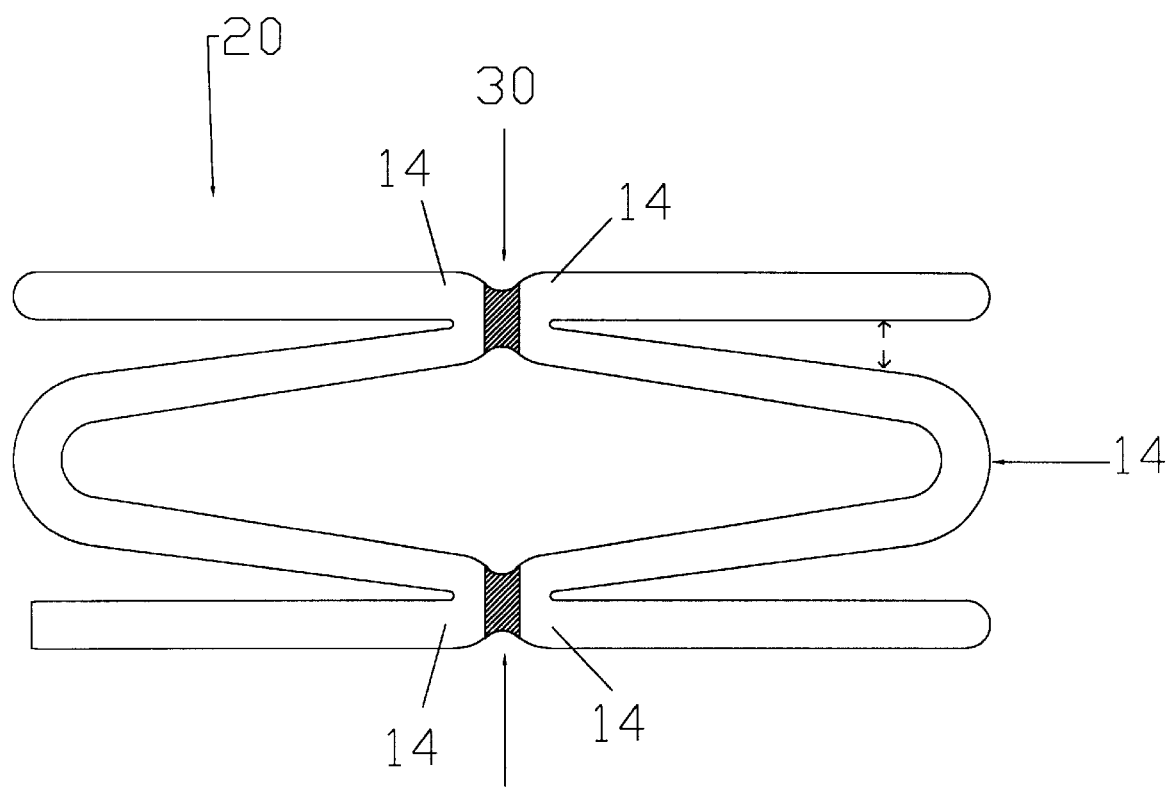
FIG. 3A is an enlarged side sectional view of the assembled connected stent of FIG. 1, prior to deployment and expansion, taken along lines 2—2 and showing the welded crown areas.

Referring now to FIGS. 2 and 3A, a connected stent 20 is formed from two or more stent segments 10 by aligning the stent segments 10 end to end so that corresponding crowns 14 are adjacent. The connected stent 20 is formed by a weld 30 between at least one set of corresponding axial turns 14 or crowns on the adjacent stent segments 10. Any welding or rigid joint forming material suitable for implantation into the body may be used, and it is preferred to use the same stainless steel for both the stent segments 10 and the welds 30. The welds 30 are approximately the same width as the cross-sections of the crowns 14 and sections 13. The length of the welds 30 is selected so that approximately one quarter of the diameter of the crown 14 is not welded. The welds 30, which are substantially rigid, are made as small as possible to reduce the mass and maintain the flexibility of the connected stent 20, the segments 10 thereof which are inherently somewhat flexible.

Figure 5:
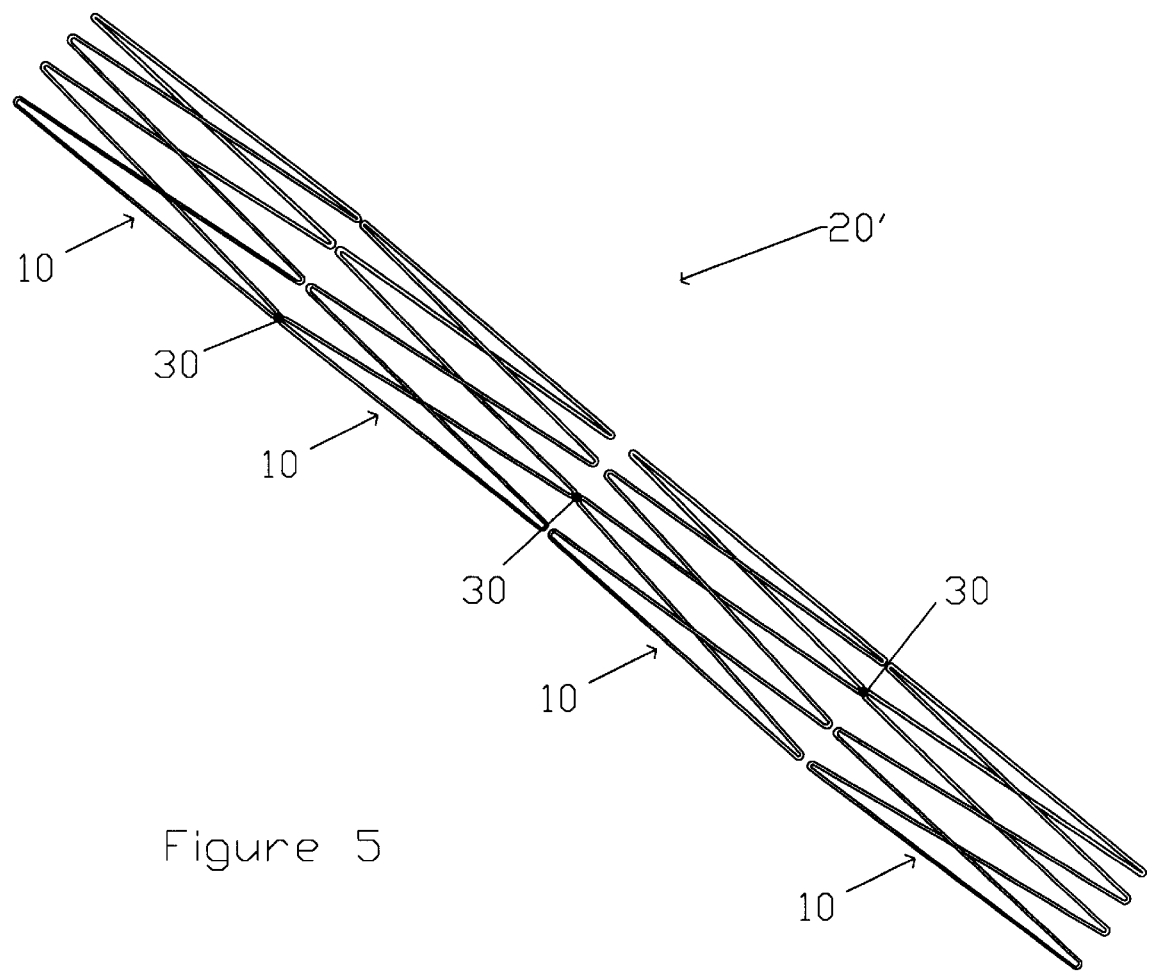
FIG. 5 is a side view of a preferred connected stent having four stent segments connected by a pattern of welds spiraling around the connected stent.

As shown in FIG. 2, welds 30 may be placed at each adjacent crown 14 area around the cylindrical connected stent, and four welds 30 are shown. Alternatively as best shown in FIG. 5, welds 30 may be placed at only one adjacent crown pair between two adjacent stent sections 10. FIG. 5 shows a connected stent 20' having four stent segments 10. The welds 30 form a spiral pattern around the cylindrical stent 20'. The spiral pattern shown in FIG. 5, or an alternating pattern, reduces the number of welds 30 thereby maintaining the flexibility of the connected stent 20'.

It will be recognized by those skilled in the art that the number of axial turns (crowns 14) in each stent segment 10 may vary, generally between two and ten with the optimum being four to seven, and that the number of welds 30 may vary accordingly. At least one weld 30 is required to connect two stent segments 10, and it is preferable to space welds in a balanced fashion in the spiral or alternating configuration. Alternatively, the welds 30 may be selectively placed to more easily selectively configure a connected stent to the contours of the vessel to be treated.

Figure 3B:
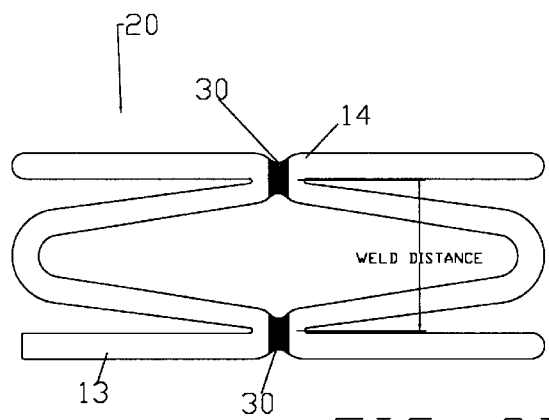
FIG. 3B shows the section view in its deployed configuration.
Figure 4A:
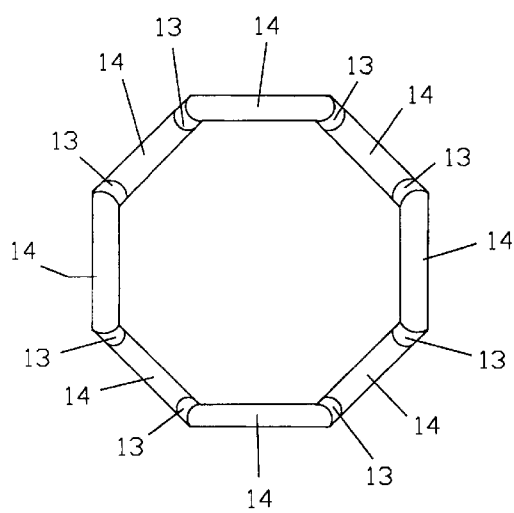
FIG. 4A is an end view of the connected stent prior to deployment and expansion.
Figure 4B:
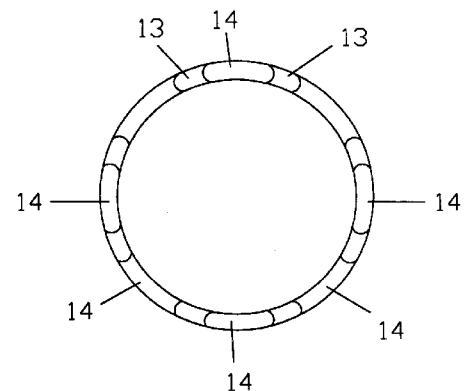
FIG. 4B is an end view of the deployed and expanded connected stent.

FIG. 3B shows the increased spacing between the straight sections 13 following application of a radially expansive force to expand the connected stent 20 into its deployment position. A comparison of FIG. 3A and 3B shows that expansion causes the angle of the crown 14 to increase, and causes the distance between welds 30 to increase. The comparison between the non-expanded and the expanded configuration may also be seen in FIG. 4A (non-expanded) and FIG. 4B (expanded). The crowns 14 can be seen to permit each stent segment 10 to be compressed or expanded over a wide range while still maintaining a significant mechanical force, such as required to prevent a vessel from restenosing.

The minimum length of the connected stent 20 or 20' is determined in large measure by the size of the vessel into which the stent 20 will be implanted. The connected stent 20 will preferably be of sufficient length to maintain its axial orientation with the vessel without shifting under the hydraulics of blood flow (or other fluid flow in different types of vessels), while also being long enough to extend across at least a significant portion of the affected area. At the same time, the connected stent should be short enough as to not introduce unnecessarily large amounts of material as might cause undue thrombosis. Typical cardiovascular vessels into which the connected stent 20 might be implanted range from 1.5 millimeters to six millimeters in diameter, and corresponding connected stents 20 may range from approximately 4 millimeters to four centimeters in length.

Due to the conformability of the single weld connected stent, not only can varying lesion lengths be treated, but curved vessels and multi-curved vessels may also be treated.

Once the configuration of the connected stent has been selected and the stent is welded to form the selected configuration, the connected stent may be crimped onto a balloon of a balloon catheter device for delivery to the affected region of a vessel such as a coronary artery. Once the balloon is in place across the lesion, using conventional imaging techniques and radiopaque dyes, the balloon may be inflated, again substantially in a conventional manner, to deploy the connected stent. In selecting a balloon, it is helpful to ensure that the balloon will provide radially uniform inflation so that the connected stent will expand equally along each of the segments. The inflation of the balloon causes the expansion of the stent. The amount of inflation, and commensurate amount of expansion of the connected stent, may be varied as dictated by the lesion itself, making the connected stent of the present invention particularly flexible in the treatment of chronic restenosis.

Because of the inflation of the balloon, the lesion in the vessel is compressed, or cracked, and the lumen is expanded accordingly when the wall of the vessel to pressed outwardly radially. At the same time, the plaque deposited within the intima of the vessel is displaced and thinned, and the stent is embedded in the plaque or other fibrotic material adhering to the intima of the vessel.

Following inflation of the balloon and expansion of the connected stent within the vessel, the balloon is deflated and removed. The exterior wall of the vessel attempts to return to its original shape through elastic recoil. The stent, however, remains in its expanded form within the vessel, and prevents further restenosis of the vessel. The stent maintains an open passageway through the vessel, so long as the tendency toward restenosis is not greater than the mechanical strength of the stent. Because of the low mass of the support device of the present invention, thrombosis is less likely to occur. Ideally, the displacement of the plaque deposits and the implantation of the stent will result in a smooth inside diameter of the vessel.

While the primary application for the connected stent is presently believed to be treatment of cardiovascular disease such as atherosclerosis or other forms of coronary narrowing, the stent of the present invention may also be used for treatment of narrowed vessels in the kidney, leg, carotid, or elsewhere in the body. In such other vessels, the size of the connected stent may need to be adjusted to compensate for the differing sizes of the vessel to be treated.

While this invention has been described in connection with preferred embodiments thereof, it is obvious that modifications and changes therein may be made by those skilled in the art to which it pertains without departing from the spirit and scope of the invention. For instance, other stents may be axially aligned and connected by welds without departing from the spirit and scope of the invention. Accordingly, the aspects discussed herein are for illustration only and should not limit the scope of the invention herein which is defined by the claims.

What is claimed is:

1. A connected endovascular support device for implantation in a vessel within the human body comprising:
   at least two unitary wire-like generally circular members each bent to form a plurality of substantially straight, non-overlapping segments connected at axial bends;
   the at least two generally circular members having at least one pair of aligned axial bends; and
   the at least two circular members connected by at least one substantially rigid joint at least one pair of aligned axial bends.

2. The connected support device of claim 1 wherein all axial bends are aligned and connected by a substantially rigid joint.

3. The connected support device of claim 1 wherein selected aligned axial bends are connected by substantially rigid joints to form a generally spiral pattern of joints around the support device.

4. The connected support device of claim 1 wherein selected aligned axial bends are connected by substantially rigid joints to form an alternating pattern of joints around the support device.

5. The connected support device of claim 1 wherein the substantially rigid joint is a weld.

6. A connected stend apparatus comprising:
- at least three adjacent short discrete stent members, each formed of a plurality of substantially straight, non-overlapping segments integrally connected at axial bends;
- at least one pair of aligned axial bends between adjacent stent members; and
- said at least one pair of aligned axial bends between adjacent stent members being connected by a substantially rigid joint.

7. The connected stent according to claim 6 wherein said connected aligned axial bends form a generally spiral pattern of substantially rigid joints around the stent apparatus.

8. The connected stent according to claim 6 wherein said connected aligned axial bends form an alternating pattern of substantially rigid joints around the stent.

9. The connected stent according to claim 6 wherein all axial bends between adjacent stent members are aligned.

10. The connected stent according to claim 9 wherein all aligned axial bends are connected by substantially rigid joints.

11. The connected stent according to claim 6 wherein the substantially rigid joint is a weld.

12. The connected stent according to claim 6 wherein the stent members have a generally ellipsoidal cross-sectional shape.

13. The connected stent according to claim 6 wherein the stent members have a generally circular cross-sectional shape.

14. A connected stent apparatus comprising:
- a first generally tubular member having first and second ends and comprising a plurality of substantially straight, non-overlapping segments connected at axial bends;
- a second generally tubular member having first and second ends and comprising a plurality of substantially straight, non-overlapping segments connected at axial bends;
- wherein one axial bend at the first end of the first generally tubular member is connected by a substantially rigid joint to one axial bend of the first end of the second generally tubular element; and
- wherein said first and second generally tubular members are non-overlapping.

* * * * *